United States Patent [19]
Kerins et al.

[11] Patent Number: 5,985,396
[45] Date of Patent: Nov. 16, 1999

[54] FLUSHABLE RELEASE LINERS AND METHODS OF MAKING THE SAME

[75] Inventors: John E. Kerins, Neenah; Yihua Chang, Appleton; William S. Pomplun, Neenah, all of Wis.

[73] Assignee: Kimberly-Clark Worldwide, Inc., Neenah, Wis.

[21] Appl. No.: 08/978,031

[22] Filed: Nov. 25, 1997

[51] Int. Cl.$^6$ ........................................................ B32B 9/04
[52] U.S. Cl. ........................ 428/41.8; 428/40.1; 428/364; 428/352; 428/335; 428/421; 604/364
[58] Field of Search ................................. 428/40.1, 41.8, 428/352, 335; 604/364

[56] References Cited

U.S. PATENT DOCUMENTS

| | | |
|---|---|---|
| H1340 | 7/1994 | Yetter et al. . |
| 3,515,582 | 6/1970 | Blackley ................................. 117/143 |
| 3,550,592 | 12/1970 | Bernardin . |
| 3,554,788 | 1/1971 | Fechillas . |
| 3,559,650 | 2/1971 | Larson . |
| 3,575,173 | 4/1971 | Loyer ..................................... 128/290 |
| 3,636,952 | 1/1972 | George . |
| 3,654,928 | 4/1972 | Duchane . |
| 3,707,430 | 12/1972 | Costanza et al. . |
| 3,855,052 | 12/1974 | Mestetsky ............................... 161/167 |
| 3,881,041 | 4/1975 | Glienke . |
| 4,097,943 | 7/1978 | O'Connell . |
| 4,151,344 | 4/1979 | Doss et al. ................................ 528/34 |
| 4,171,397 | 10/1979 | Morrow .................................. 428/195 |
| 4,186,233 | 1/1980 | Krajewski et al. . |
| 4,229,239 | 10/1980 | Arai . |
| 4,269,650 | 5/1981 | Arai . |
| 4,282,054 | 8/1981 | Mattor et al. ........................... 156/289 |
| 4,333,464 | 6/1982 | Nakano . |
| 4,348,293 | 9/1982 | Clarke et al. ............................ 252/90 |
| 4,372,311 | 2/1983 | Potts . |
| 4,386,135 | 5/1983 | Campbell et al. ...................... 428/447 |
| 4,416,791 | 11/1983 | Haq . |
| 4,536,435 | 8/1985 | Magnotta ................................ 428/200 |
| 4,588,400 | 5/1986 | Ring et al. . |
| 4,654,395 | 3/1987 | Schulz . |
| 4,655,868 | 4/1987 | Hefele . |
| 4,705,584 | 11/1987 | Lauchenauer . |
| 4,731,143 | 3/1988 | Cross . |
| 4,900,554 | 2/1990 | Yanagibashi et al. . |
| 4,959,264 | 9/1990 | Dunk et al. ............................. 428/331 |
| 5,009,647 | 4/1991 | Cross et al. ............................. 604/332 |
| 5,009,652 | 4/1991 | Morgan et al. . |
| 5,061,559 | 10/1991 | Ogusi et al. ............................ 428/343 |
| 5,071,648 | 12/1991 | Rosenblatt . |
| 5,082,706 | 1/1992 | Tangney ................................... 428/40 |
| 5,198,299 | 3/1993 | Kato et al. .............................. 428/240 |
| 5,300,358 | 4/1994 | Evers . |
| 5,332,607 | 7/1994 | Nakamura et al. ....................... 428/40 |
| 5,391,423 | 2/1995 | Wnuk et al. ............................ 428/217 |
| 5,405,475 | 4/1995 | Kraft et al. . |
| 5,468,807 | 11/1995 | Tsurutani et al. . |
| 5,472,518 | 12/1995 | Patnode et al. . |
| 5,509,913 | 4/1996 | Yeo . |
| 5,529,830 | 6/1996 | Dutta . |
| 5,569,348 | 10/1996 | Hefele . |
| 5,584,800 | 12/1996 | Scholz et al. . |
| 5,603,691 | 2/1997 | Scholz et al. . |
| 5,691,022 | 11/1997 | Knauf ..................................... 428/40.1 |
| 5,700,571 | 12/1997 | Logue et al. ........................... 428/352 |
| 5,716,685 | 2/1998 | Kumar et al. .......................... 428/40.1 |

FOREIGN PATENT DOCUMENTS

| | | |
|---|---|---|
| 0 461 484 | 12/1991 | European Pat. Off. . |
| 0 479 404 | 4/1992 | European Pat. Off. . |
| 0-532 805 A1 | 3/1993 | European Pat. Off. . |
| 63-46233 | 2/1988 | Japan . |
| 5-200375 | 8/1993 | Japan . |
| 5-228172 | 9/1993 | Japan . |
| 5-293070 | 11/1993 | Japan . |
| 7-70525 | 3/1995 | Japan . |
| WO 94/23769 | 10/1994 | WIPO . |
| WO 96 20831 | 7/1996 | WIPO . |
| WO 97 18082 | 5/1997 | WIPO . |
| WO 99 08727 | 2/1999 | WIPO . |

OTHER PUBLICATIONS

JP 06 100845, Apr. 12, 1994, Abstract.
JP 07 003699, Jan. 6, 1995, Abstract.
JP 06 126901, May 10, 1994, Abstract.
JP 06 134910, May 17, 1994, Abstract.

*Primary Examiner*—David W. Wu
*Assistant Examiner*—Caixia Lu-Rutt
*Attorney, Agent, or Firm*—Jones & Askew, LLP

[57] ABSTRACT

The present invention is directed to a flushable water-sensitive film, which maintains its integrity and strength when in use, but disperses when place in contact with water, such as in a conventional sink or toilet. Moreover, the present invention is directed to a flushable release liner, which performs like conventional release papers, but adds the convenience of disposal by flushing in a sink or toilet. The present invention is also directed to products, which contain a flushable water-sensitive film or release liner.

19 Claims, No Drawings

FLUSHABLE RELEASE LINERS AND METHODS OF MAKING THE SAME

FIELD OF THE INVENTION

The present invention is directed to a flushable release liner. The flushable release liner is formed by applying a release coating onto at least one surface of a water-sensitive film. The flushable release liner maintains its structural integrity and strength when in use, but disperses when placed in contact with water, such as in a conventional sink or toilet. Moreover, the present invention is directed to products, including flushable and non-flushable products, which contain the flushable release liner.

BACKGROUND OF THE INVENTION

Disposable products have dramatically altered modern lifestyle, adding great convenience to everyday living for society. Such products generally are relatively inexpensive, sanitary and quick and easy to use. Disposal of such products, however, increasingly is a problem as landfills close and incineration contributes to urban smog and pollution. Consequently, there is an urgent need for disposable products that can be disposed of without dumping or incineration. An ideal disposal alternative would be the use of municipal sewage treatment and private residential septic systems. Products suited for disposal in sewage systems that can be flushed down a conventional toilet are termed "flushable." An essential feature of flushable products is that they must have sufficient strength for their intended use, yet lose structural integrity upon contact with water.

Numerous attempts have been made to produce flushable materials that retain their integrity and strength for their intended purpose yet can be disposed of via flushing in conventional toilets. One approach to producing a flushable product is to limit the size of the product so that it will readily pass through plumbing without causing obstructions or blockages. Such products often have high wet strength and do not disintegrate during flushing. Examples of this type of product include wipes such as baby wipes. This approach to flushability suffers the disadvantage, however, of being restricted to small sized articles. Many current flushable products are limited to such small articles.

Numerous consumer products, which were formerly unable to be disposed of in a conventional toilet, are made flushable today. Such products include water-soluble films, wipes, tampon applicators, etc. However, many consumer products have remained unflushable.

One such product that has remained unflushable to date is release liners. Release liners are used to temporarily cover an adhesive layer before use in many personal care products. The release liner provides protection for the adhesive layer against exposure to materials, which might negatively effect the ability of the adhesive strip to adhere to a desired substrate and provides protection against undesired, premature adhesion to a substrate. Conventional release liners comprise a paper substrate coated with a release coating. The release coating is formulated to provide very little adhesion of the coated paper to any other substrate, particularly pressure-sensitive, hot-melt adhesives, so the release liner may be easily removed from the adhesive strip without disturbing the adhesive strip. Typically, release coatings comprise a silicone-containing polymeric material.

Release liners are used in many personal care products. For example, many sanitary napkins have an adhesive strip on the backside of the napkin (the napkin surface opposite to the body-contacting surface) to fix the napkin to an undergarment and hold the napkin in place against the body. Before use, the adhesive strip is protected with a peelable release liner. Once removed, the peelable release liner must be discarded. Since peelable release liners are typically silicone-coated paper, the release liners do not readily disperse in water; consequently, disposal options are limited to depositing the release liner in a trash receptacle. Although disposing of conventional release liners in a toilet would be convenient to the consumer, such disposal potentially creates blockages in the toilet.

What is needed in the art is a flushable release sheet, which can be discarded and then flushed in a conventional toilet. Such a flushable release liner would offer convenience to the consumer, and not cause problems such as blockages in the sewage transport process

SUMMARY OF THE INVENTION

The present invention is directed to a flushable release liner comprising a thin discontinuous release coating on at least one surface of a water-sensitive film. The coated water-sensitive film functions like conventional release papers currently used. Conventional release papers comprise a peelable coated paper, which covers the adhesive strip on, for example, a feminine sanitary napkin. Unlike conventional release papers, the coated water-sensitive film of the present invention rapidly loses integrity and strength when discarded in a conventional toilet or sink. Without the support of the water-sensitive film, the thin discontinuous release coating readily breaks up under the force of flushing water in a toilet or water flow in a sink. The two-layer structure of the flushable release liner offers the performance of a paper-based release liner with the additional option of disposal in a toilet or sink and of potentially lower cost.

The present invention is also directed to a method of preparing a ilushable release sheet. The method comprises coating a thin discontinuous layer of polymer having release characteristics onto a base film, wherein the base film comprises a water-sensitive polymer. When dry, the coated water-sensitive film displays mechanical features comparable to a conventional coated paper liner. The base film itself may be manufactured, taking into consideration variables such as film thickness, molecular weight, and blending additives, to control the functional similarity of the plastic film to a coated paper liner. Desirably, the discontinuous coating is present on the film surface in the form of a discrete pattern of dots, wherein the dots are coated onto the film by a hot melt screen printing process. The discontinuous polymeric coating controls the release characteristics of the plastic film. The discontinuous coating is formulated to provide very little adhesion to many substrates, particularly pressure-sensitive, hot-melt adhesives, so that the coating may be easily removed from an adhesive strip without disturbing the adhesive strip, while having high adhesion to the water-sensitive substrate. The coating formulation ensures that the coated water-sensitive film peels at the surface of the release coating, not at the interface between the coating and the water-sensitive base film.

The present invention is also directed to articles containing the flushable release liner. Specifically, the flushable release liners of the present invention are useful in connection with a variety of products, and especially absorbent products such as sanitary napkins, panty liners, diapers, dressings and the like. Although the release liner of the present invention finds particular use in the above-mentioned products, the concept of a flushable release liner has potential for any other application requiring a release material.

The present invention provides a mechanism for eliminating disposal problems associated with various consumer products. A nonlimiting detailed description of the invention and examples of specific embodiments are provided below.

DETAILED DESCRIPTION OF THE INVENTION

The present invention is directed to a flushable release liner comprising a thin discontinuous release coating on at least one surface of a water-sensitive film. As used herein, a "release liner" refers to a layer which adheres to and protects an adhesive on a product, until the product is to used, at which time the layer is removed to expose the adhesive. The coated water-sensitive film of the present invention functions like conventional release papers currently used. However, unlike conventional release papers, the coated water-sensitive film of the present invention is "flushable." As used herein, the term "flushable" describes a product which rapidly loses integrity and strength when discarded in a conventional sink or toilet. The flushable feature of the coated water-sensitive film of the present invention comes from the water-sensitivity of the base film and the discontinuity of the thin release coating. When immersed in water, the uncoated side of the base film readily wets and weakens. The water-sensitive film quickly loses integrity and strength when exposed to water. When the substrate layer loses its mechanical integrity, the pieces of discontinuous release coating readily disperse under the flushing force of the toilet or water flow in the sink.

The coated water-sensitive film of the present invention is prepared by any process wherein a thin discontinuous layer of polymer, having release characteristics, is coated onto at least one surface of a water-sensitive film, such as a polyethylene oxide (PEO) film. Suitable coating processes include, but are not limited to, solvent-base coating and hot-melt coating. Suitable solvent-base coating techniques include, but are not limited to, spray coating and ink jet printing. Suitable hot-melt coating techniques include, but are not limited to, slot coating, screen coating, spray coating, swirl coating, and gravure coating. Desirably, the coating process is a hot-melt screen coating process. The discontinuous coating is desirably present on the film surface in the form of a discrete pattern of dots. At least a portion of the surface area of the water-sensitive film is left uncoated so that the coated water-sensitive film remains flushable. One coating process is described below.

Molten "release polymer" is delivered from a melting tank through a heated hose to a slot die located inside a screen cylinder. As used herein, the term "release polymer" describes a polymer which possesses release characteristics. The temperature of the melting tank, hose and screen cylinder may vary depending upon the melt rheology of the release polymer in the coating process. The molten polymer is distributed uniformly on the inner wall of the rotating screen cylinder, and then applied through screen holes, as discrete dots, directly onto the water-sensitive film, or alternatively, onto a carrier substrate outside and adjacent to the screen cylinder. The screen and film/carrier substrate may move at the same or different speeds depending upon the distortion of dot shape desired. When the screen and film/carrier substrate travel at the same speed, symmetrical dots are produced. When the screen and film/carrier substrate travel at different speeds, dots elongated in the machine direction are produced. Elongation of the dots may result in bridging of some or all of the dots. Line speed may vary depending upon the "open time" of the release polymer. As used herein, the "open time" of a polymer refers to the amount of time required for the polymer to loose its tackiness.

In a transfer coating process, the coated carrier substrate moves further through the process and comes into contact with the water-sensitive film, which is properly aligned with the coated carrier substrate. The coating is transferred from the carrier substrate to the water-sensitive film under pressure as the film and carrier substrate pass through a nip roll. The dots spread out as a result of the nip pressure during the transfer process. The degree of spreading depends on the pressure, open time of the release polymer resin, and the coating speed. Desirably, spreading should minimize the gap between dots without coalescence of the dots. In practice, optimum dot spacing is achieved by adjusting processing factors which include, but are not limited to, the release polymer, the coating temperature, the screen pattern, the resin flow rate, screen speed, line speed, and the pressure applied at the nip roll.

In either the direct coating process or the transfer coating process, the adhesion of the dots to the water-sensitive film should be greater than the adhesion of the dots to the screen (direct coating) or the carrier substrate (transfer coating). The choice of release polymer should take into consideration the desired adhesion properties of the release polymer. The release polymer should have good adhesion to the water-sensitive substrate. Suitable release polymers for use in the present invention include any processible polymer with appropriate melt rheology, release characteristics and adhesion properties for application by the above-described hot melt screen coating process. Suitable release polymers include, but are not limited to, polyolefins, fluoropolymers, and silicones.

One or more of the release polymers above may be combined to form the discontinuous coating of the water-sensitive film. Further, the release polymer may contain one or more of the following additives including, but not limited to, compatibilizers, processing aids, plasticizers, tackifiers, detackifiers, slip agents, and anti-microbial agents, as fabricating agents or as modifiers depending on the specific properties desired in the coating and the final product. The discontinuous coating should be formulated to provide little adhesion to a variety of substrates, particularly pressure-sensitive, hot-melt adhesives, so that the coating may be easily removed from an adhesive strip without disturbing the adhesive strip, while having high adhesion to the water-sensitive substrate. The coating formulation ensures that the coated water-sensitive film peels at the surface of the release coating, not at the interface between the coating and water-sensitive base film.

Desirably, the release polymer is a polyalphaolefin having a melt viscosity of about 400 to about 10,000 cps at 190° C. Suitable polymers include, but are not limited to, amorphous ethylene-propylene copolymers and ethylene-butylene copolymers. Particularly suitable polymers are manufactured by the U.S. Rexene Company under the tradename REXTAC®. Two REXTAC® resins, RT2330 and RT2730, are particularly suitable for the present invention. In a further embodiment, one or more REXTAC® resins are blended with a low molecular weight, highly branched polyolefin to reduce the tackiness of the release polymer coating. Desirably, the highly branched polyolefin has a number-average molecular weight ($M_n$) of less than about 2800. A particularly suitable low molecular weight, highly branched polyolefin, VYBAR® 253 ($M_n$=520), is manufactured by the Petrolite Corporation. Blends of REXTAC® resin and VYBAR® 253 provide good results as release coating materials. Desirably, the ratio of REXTAC® resin to VYBAR® 253 is from about 100/0 wt/wt to about 70/30 wt/wt. More desirably, the ratio of REXTAC® resin to VYBAR® 253 is from about 98/2 wt/wt to about 75/25 wt/wt. Most desirably, the ratio of REXTAC® resin to VYBAR® 253 is from about 95/5 wt/wt to about 80/20 wt/wt. Particularly useful blends are RT2330/VYBAR® 253 (95/5 wt/wt) and RT2730/VYBAR® 253 (80/20 wt/wt).

Desirably, the discontinuous release coating is coated onto the water-sensitive film in the form of a plurality of dots. The dots may have any shape desired. Suitable shapes include, but are not limited to, circles, squares, rectangles, triangles, and hexagons. Desirably, the dot shape allows uniform, discontinuous coverage of the film and minimal spacing between adjacent dots. More desirably, the dots are present as substantially discontinuous interengaged shapes of release polymeric material, resembling pieces of a jigsaw puzzle, adhered to and uniformly covering the water-sensitive film surface. As used herein, the phrase "substantially discontinuous" describes a coating wherein the dots are completely distinct from one another with no overlapping of the dots, and also a coating wherein some overlapping of the dots takes place. As used herein, the term "interengaged" describes the relationship of the dots on the film surface such that the exposed surface area of the film is minimized.

Dot size and thickness may vary greatly depending upon the end use of the coated water-sensitive film-containing product. Desirably, dot dimensions should be less than about 100 mm for flushable films to avoid potential clogging in conventional toilets. Dot thickness should be minimized when possible to reduce product cost. Desirably, the discontinuous release coating has a coating thickness of less than about 1.0 mil. (25.4 micrometers). More desirably, the discontinuous release coating has a coating thickness of less than about 0.6 mil. (15.2 micrometers). Most desirably, the discontinuous release coating has a coating thickness of less than about 0.2 mil. (5.1 micrometers). However, the coating should be thick enough to provide a continuous pattern of dots along the film surface.

The carrier substrate used in the above-described process may be any substrate which can transfer the discontinuous release coating to the water-sensitive film. Suitable carrier substrates display little or no adhesion with the release coating relative to the adhesion between the water-sensitive film and the release coating. Suitable carrier substrates include, but are not limited to, release paper, release films, and release-coated substrates such as fabrics and/or belts. Desirably, the carrier substrate is a release paper. More desirably, the carrier substrate is an AKROSIL® High Release Paper.

Water-sensitive films for use in the present invention include any water-sensitive film capable of withstanding the above-described coating processes. As used herein, the phrase "water-sensitive film" describes films, which lose integrity over time when in the presence of water and includes, but is not limited to, water-soluble films and water-dispersible films. Suitable water-sensitive films have sufficient strength and adhesion properties for use in the above-described process. Suitable polymers include, but are not limited to, polyalkylene oxides, such as polyethylene oxide (PEO) and ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), and poly (2,4-dimethyl-6-triazinyl ethylene).

The water-sensitive film of the present invention may be made entirely of water-sensitive polymeric material or may contain water-sensitive as well as water-insoluble materials so long as the film disperses in water, such as in a conventional sink or toilet. Additionally, water-sensitive films may also be made by combining various different types of water-sensitive film materials. In some embodiments, it may be desirable to employ one or more additives into the water-sensitive film material including, but not limited to, compatibilizers, processing aids, plasticizers, tackifiers, detackifiers, slip agents, and anti-microbial agents, as fabricating agents or as modifiers depending on the specific properties desired in the film and the final product.

Desirably the water-sensitive film of the present invention comprises a polyalkylene oxide film or a polyvinyl alcohol film. More desirably, the water-sensitive film of the present invention comprises a polyethylene oxide film, an ethylene oxide/propylene oxide copolymer film or a polyvinyl alcohol film. More desirably, the water-sensitive film of the present invention comprises a polyethylene oxide film or a polyvinyl alcohol film. The polyethylene oxide film is the most desirable film for the transfer coating procedure, while the polyvinyl alcohol film is the most desirable film for the direct coating procedure.

The thickness of the water-sensitive film may vary greatly depending upon the end use of the coated water-sensitive film and/or products containing the coated water-sensitive film. Film thickness should be minimized when possible to reduce product cost and to reduce the time necessary for the film to disperse, especially in the case of flushable products. Desirably, the water-sensitive film thickness will be less than about 2.0 mil (50.8 micrometers). More desirably, the water-sensitive film thickness will be from about 0.1 mil (2.5 micrometers) to about 1.4 mil (35.6 micrometers). Most desirably, the water-sensitive film thickness will be from about 0.1 mil (2.5 micrometers) to about 0.5 mil (12.7 micrometers).

With release characteristics and adhesion properties, the coated water-sensitive film of the present invention finds applicability in a variety of articles. Specifically, the flushable release liners of the present invention are useful in connection with a variety of products, and especially absorbent products such as sanitary napkins, diapers, dressings and the like. Although the release liner of the present invention finds particular use in the abovementioned products, the concept of a flushable release liner has potential for any other applications wherein a release liner is used.

Those skilled in the art will readily understand that the coated water-sensitive film of the present invention may be advantageously employed in the preparation of a wide variety of products designed to contain at least one component having a release surface. Such products may comprise only the coated water-sensitive film or may comprise a coated water-sensitive film in combination with one or more additional layers such as coatings, films, fabrics, etc. Although the coated water-sensitive film of the present invention is particularly suited for release liners, the coated water-sensitive film of the present invention may be advantageously employed in the preparation of a wide variety of consumer products other than release liners.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

A release liner was made by the following process. A release coating comprising a 100 wt % coatinggrade polyalphaolefin, REXTAC® RT2330 (U.S. Rexene Company), was coated onto a high release paper using a 40 mesh screen, and subsequently transferred to a PEO film under the following conditions: tank temperature, 335° F.; grid temperature, 345° F.; hose temperature, 345° F.; die temperature, 354° F.; screen speed, 35 ft/min.; and line speed, 24 ft/min. The base film of PEO, roughly 1.2 mil (30.5 micrometers) thick, was prepared from resin compounded at Planet Polymer (San Diego, Calif.). The blend was applied the PEO film to produce a final coating thickness of about 0.8 mil (20.3 micrometers). Higher line speed facilitated the spreading of dots because of less temperature drop before the nip at pressure. At a line speed of 25 ft/min., coalescence of the dots started to occur.

The average spacing between dots on the release paper was about 0.2 mm. The resulting release liner had an average spacing between dots of about 0.1 mm the PEO film. However, the resulting discontinuous coating was tacky due to the nature of the REXTAC® RT2330 resin.

EXAMPLE 2

A release liner was made as in Example 1, except the release coating comprised a blend of 95 wt % REXTAC® RT2330 resin and 5 wt % of a low molecular weight paraffin wax, VYBAR® 253 (Petrolite Polymers). The release coating was coated onto a high release paper using a 40 mesh screen, and subsequently transferred to a PEO film under the following conditions: tank temperature, 335° F.; grid temperature, 345° F.; hose temperature, 345° F.; die temperature, 354° F.; screen speed, 35 ft/min.; and line speed, 24 ft/min. The base film of PEO, roughly 1.2 mil (30.5 micrometers) thick, was prepared from resin compounded at Planet Polymer. The blend was applied the PEO film to produce a final coating thickness of about 0.8 mil (20.3 micrometers). Higher line speed facilitated the spreading of dots because of less temperature drop before the pressure nip. At a line speed of 25 ft/min., coalescence of the dots started to occur.

The average spacing between dots on the release paper was about 0.2 mm. The resulting release liner had an average spacing between dots of about 0.1 mm the PEO film. The resulting discontinuous coating was significantly less tacky compared with the 100 wt % REXTAC® RT2330 resin coating.

EXAMPLE 3

To further reduce the gap between dots, a 50 mesh screen, which has less space between holes, was used to produce a release liner using identical components and process conditions as used in Example 2. The dots produced with the 50 mesh screen were smaller and did not coalesce. An increased line speed of 25 ft/min., while maintaining the screen speed at 35 ft/min., resulted in some pulling of dots, but no significant improvement in coalescence of dots. An increase in all the temperatures by 10 Fahrenheit degrees showed no difference in dot coalescence.

EXAMPLE 4

A release liner was made by the following process. A release coating comprising 100 wt % hydrophobic polymer REXTAC® RT2730 (U.S. Rexene Company) was coated on a high release paper, using a 40 mesh screen, and subsequently transferred to a PEO film under the following conditions: tank temperature, 301° F.; grid temperature, 303° F.; hose temperature, 309° F.; die temperature, 312° F.; screen speed, 35 ft/min.; and line speed, 25 ft/min. The base film of PEO, roughly 1.2 mil (30.5 micrometers) thick, was prepared from resin compounded at Planet Polymer. The coating was applied the PEO film to produce a final coating thickness of about 0.8 mil (20.3 micrometers).

The resulting release liner had an average spacing between dots of about 0.2 mm the PEO film. However, the resulting discontinuous coating was tacky due to the nature of the REXTAC® RT2730 resin.

EXAMPLE 5

A release liner was made as in Example 4, except the release coating comprised a blend of 80 wt % hydrophobic polymer REXTAC® RT2730 and 20 wt % VYBAR® 253. The release coating was coated on a high release paper, using a 40 mesh screen, and subsequently transferred to a PEO film under the following conditions: tank temperature, 301° F.; grid temperature, 303° F.; hose temperature, 309° F.; die temperature, 312° F.; screen speed, 35 ft/min.; and line speed, 25 ft/min. Significantly lower processing temperatures were used because of the relatively large weight percentage of VYBAR® 253. The blend had good spreading capability. The dots appeared flatter, and more coalescence was observed.

The resulting release liner had an average spacing between dots of about 0.1 mm the PEO film. The resulting discontinuous coating was significantly less tacky compared with the 100 wt % REXTAC® RT2730 resin coating.

What is claimed is:

1. A flushable laminate having release characteristics, said flushable laminate consisting essentially of:
   a water-sensitive film; and
   a substantially discontinuous release coating of polymeric material on a surface of the water-sensitive film, wherein the coating adheres to the water-sensitive film and provides release characteristics to the laminate;
   wherein the polymeric material comprises a polyalphaolefin having a melt viscosity of about 400 to about 10,000 cps at 190° C.

2. The flushable laminate of claim 1, wherein the water-sensitive film comprises polyethylene oxide, ethylene oxide-propylene oxide copolymers, polymethacrylic acids polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triaziniyl ethylene) or a combination thereof.

3. The flushable laminate of claim 2, wherein the water-sensitive film comprises polyethylene oxide, ethylene oxide-propylene oxide copolymer, polyvinyl alcohol or a combination thereof.

4. The flushable laminate of claim 1, wherein the coating further comprises at least one low molecular weight, highly branched polyolefin wherein the at least one low molecular weight, highly branched polyolefin has a number-average molecular weight of less than about 2800.

5. The flushable laminate of claim 3, wherein the water-sensitive film comprises polyethylene oxide.

6. The flushable laminate of claim 1, wherein the substantially discontinuous release coating comprises interengaged shapes of polymeric material having a s pace between the shapes.

7. The flushable laminate of claim 5, wherein the laminate is a flushable release liner.

8. The flushable laminate of claim 1, wherein the water-sensitive film has a thickness of less than about 2.0 mil (50.4 micrometers) and the coating has a thickness of less than about 1.2 mil (30.5 micrometers).

9. A flushable release liner consisting essentially of:
   a water-sensitive film; and
   a substantially discontinuous release coating of polymeric material on a surface of the water-sensitive film, wherein the coating adheres to the water-sensitive film and provides release characteristics to the liner;
   wherein the polymeric material comprises a polyalphaolefin having a melt viscosity of about 400 to about 10,000 cps at 190° C.

10. The flushable release liner of claim 9, wherein the water-sensitive film comprises polyethylene oxide, ethylene oxide-propylene oxide copolymers, polymethacrylic acid, polymethacrylic acid copolymers, polyvinyl alcohol, poly (2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene) or a combination thereof.

11. The flushable release liner of claim 10, wherein the water-sensitive film comprises polyethylene oxide, ethylene oxide-propylene oxide copolymer, polyvinyl alcohol or a combination thereof.

12. The flushable release liner of claim 9, wherein the coating further comprises at least one low molecular weight, highly branched polyolefin, wherein the at least one low molecular weight, highly branched polyolefin has a number-average molecular weight of less than about 2800.

13. The flushable release liner of clam 11, wherein the water-sinsitive film comprises polyethylene oxide.

14. The flushable release liner of claim 9, wherein the substantially discontinuous release coating comprises interengaged shapes of polymeric material having a space between the shapes.

15. The flushable release liner of claim 9, wherein the water-sensitive film has a thickness of less than about 2.0 mil (50.4 micrometers) and the coating has a thickness of less than about 1.2 mil (30.5 micrometers).

16. A product comprising:
   a flushable water-sensitive laminate having release characteristics, wherein the flushable water-sensitive laminate comprises a water-sensitive film and a substantially discontinuous release coating of polymeric material on a surface of the water-sensitive film, wherein the coating adheres to the water-sensitive film and provides release characteristics to the laminate; and
   at least one additional layer adhered to the substantially discontinuous release coating of the laminate;
   wherein the product comprises a disposable adsorbent article, a sanitary napkin, a dressing, a panty liner, an incontinence garment, a bandage or a diaper.

17. The product of claim 16, wherein the product comprises a disposable absorbent article, said disposable article further comprising a liquid previous topsheet and a liquid impervious backsheet.

18. A method of making a flusbable laminate having release characteristics, said method consisting essentially of:
   providing a water-sensitive film; and
   applying a substantially discontinuous release coating of a polymeric material onto a surface of the water-sensitive film, wherein the coating adheres to the water-sensitive film and provides release characteristics to the laminate.

19. The method of claim 18, wherein the coating comprises at least one polyalphaolefin having a melt viscosity of about 400 to about 10,000 cps at 190° C. and at least one low molecular weight, highly branched polyolefin, wherein the at least one low molecular weight, highly branched polyolefin has a number-average molecular weight of less than about 2800.

* * * * *